United States Patent [19]

Storz

[11] Patent Number: 4,838,245

[45] Date of Patent: Jun. 13, 1989

[54] INSTRUMENT FOR THE INSERTION OF ANESTHETIC CATHETERS

[76] Inventor: Karl Storz, Auf dem Schildrain 39, 7200 Tuttlingen, Fed. Rep. of Germany

[21] Appl. No.: 188,657

[22] Filed: Apr. 29, 1988

Related U.S. Application Data

[63] Continuation of Ser. No. 524,135, Aug. 17, 1983, abandoned.

[30] Foreign Application Priority Data

Jan. 25, 1983 [DE] Fed. Rep. of Germany ... 8301892[U]

[51] Int. Cl.⁴ ............................................... A61B 1/06
[52] U.S. Cl. .......................................................... 128/6
[58] Field of Search ......................................... 128/4–8, 128/10, 11

[56] References Cited

U.S. PATENT DOCUMENTS 3,830,225  8/1974  Shimick ................................. 128/4
4,267,828  5/1981  Matsuo .................................. 128/6
4,430,996  2/1984  Bonnet .................................. 128/4

FOREIGN PATENT DOCUMENTS 0030014  6/1981  European Pat. Off. .............. 128/11

Primary Examiner—Max Hindenburg
Attorney, Agent, or Firm—Donald D. Mon

[57] ABSTRACT

An instrument for insertion into the body which includes a flexible image-transmitting element, a flexible light guide, and in some embodiments, a channel for intubation gas, which instrument contains a head for receiving a connection for the image-transmitting element. Because of their flexibility, they can variably be curved. To enable the doctor readily to follow the curvature during the insertion of the elements, an eyepiece is connected to the head by a joint or hinge. This enables the doctor to follow the varying direction during insertion of the instrument, because the angle between the head and the eyepiece member can be varied during insertion.

4 Claims, 1 Drawing Sheet

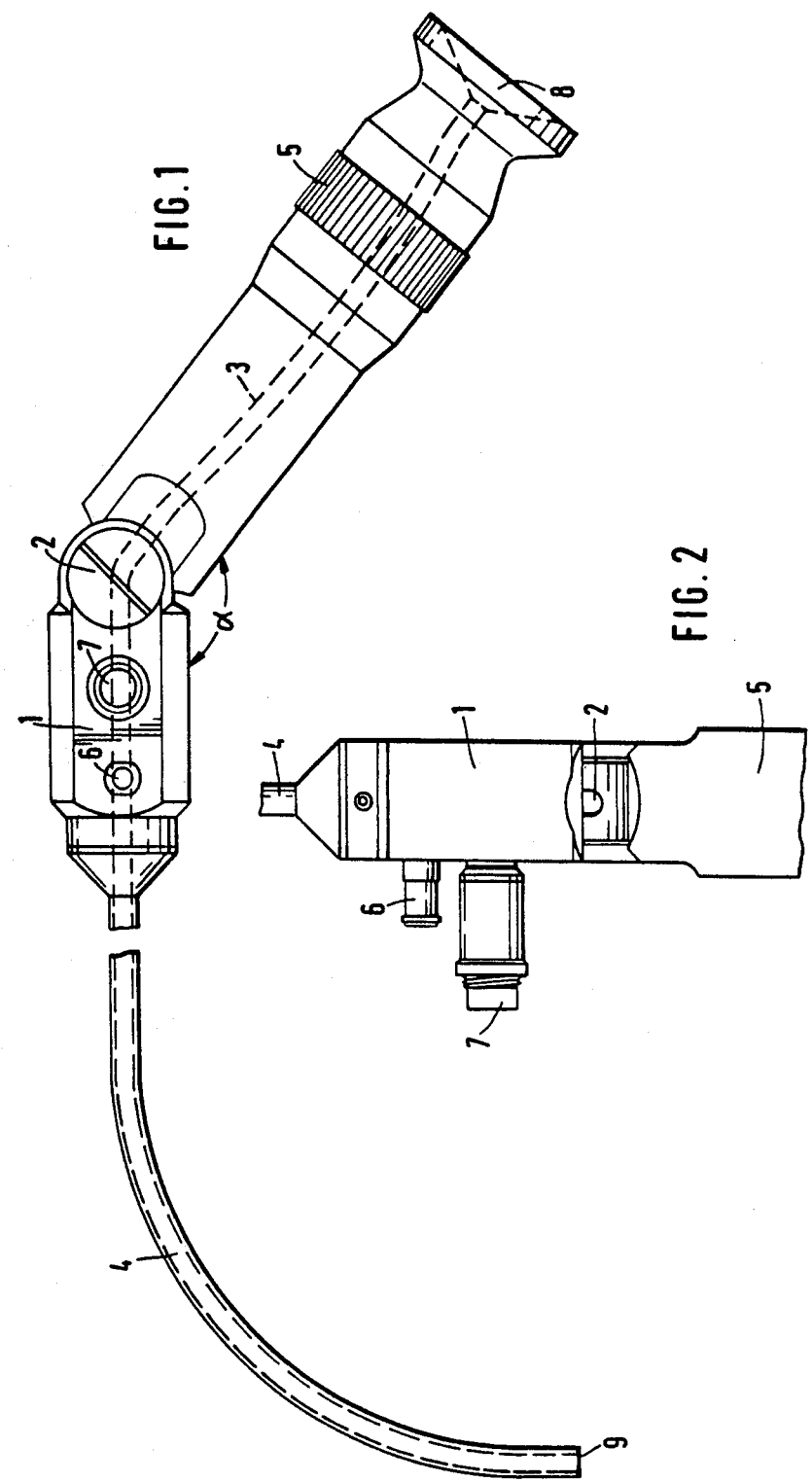

INSTRUMENT FOR THE INSERTION OF ANESTHETIC CATHETERS

This is a continuation of co-pending application Ser. No. 524,135 filed on Aug. 17, 1983, now abandoned.

FIELD OF THE INVENTION

The invention relates to an instrument for the insertion of anesthetic catheters.

BACKGROUND OF THE INVENTION

A flexible endoscope with an image-transmitting flexible element is known, which has a flexible outer tube and in which a rigid head is provided between the outer tube and the eyepiece. The distal end can be moved in various directions by means of tension and/or spring elements arranged in the endoscope shaft. Such endoscopes are commonly used for operations in the upper digestive tract. For operating the aforementioned spring elements, means such as servomotors are arranged in the head, permitting much easier manipulations by the operator (see West German Pat. No. 2,504,663).

In addition, an instrument for the insertion of anesthetic catheters into the larynx and trachea, accompanied by visual inspection with an elongated curved insertion probe is known. It also contains a glass fibre light guide. The probe is partly enveloped by the anesthetic catheter during insertion. To make this instrument much shorter and therefore more convenient, regardless of the size of the patient, the rigid insertion probe is in this case constructed with at least one partial screw turn (German Utility Model No. 82 14 033). The eyepiece is rigidly fixed to the probe, so that the doctor has considerable difficulty in following the probe or endoscope insertion direction, which varies significantly during insertion.

The problem solved by this invention is to obviate this disadvantage and enable the doctor easily to follow the varying direction of the laryngoscope during insertion.

BRIEF DESCRIPTION OF THE INVENTION

An instrument according to this invention has a flexible light guide and a flexible image-transmitting element which are joined to a head. An eyepiece receives the image-transmitting element, and is pivotally mounted to the head so the surgeon can accomodate to the changes in angulation of the light guide and transmitting element while they are being inserted into the body.

The above and other features of the invention will be fully understood from the following detailed description and the accompanying drawings, in which:

BRIEF DESCRIPTION OF THE DRAWINGS

FIG. 1 is a side view of the preferred embodiment of the invention; and

FIG. 2 is a plan view of part of the object of FIG. 1.

DETAILED DESCRIPTION OF THE INVENTION

FIG. 1 shows an intubation laryngoscope with an endoscope shaft 4, which is connected further to the right to a head 1. Endoscope shaft 4 is only partly shown and is in reality very long. It bends considerably over its length. It is made from a soft, flexible material, which can be bent to be adapted as required.

The head contains a connection 6 for intubation gas and a further connection 7 farther to the right for a moveable light guide. The light guide conveys light to the distal end of the instrument. It is not intended to transmit a coherent image. It is flexible.

According to the invention, between head 1 and eyepiece member 5 is provided a hinge 2, about which eyepiece member 5 is pivoted through an angle $\alpha$ and relative to head 1 as best shown in FIG. 1. Eyepiece 8 is located at the proximal end of eyepiece member 5. Hinge 2 is a "line-axis" hinge in the sense that it hinges on an axis around a pin shown in end view in FIG. 1 and in side view in FIG. 2 which itself has a linear central axis normal to the plane of Fig. around which the hinge pivots. A torque on the head or on the eyepiece member in the plane of FIG. 1 rotates one relative to the other in that plane through an angle $\alpha$ shown in FIG. 1. A torque exerted on the eyepiece around the central axis of the head will rotate the head.

In a conventional manner, shaft 4 contains a light guide leading to connection 7 to receive light from a light source, as well as a gas channel leading to connection 6 to receive gas from a gas source. These are conventional expedients, and are therefore not shown in detail. It is also already known that an endoscope shaft such as shaft 4 also contains an image-transmitting, flexible element 3, which transmits an image to eyepiece 8. This is shown in the form of broken lines, because it is not in fact visible in these drawings. According to the invention, the image-transmitting flexible element 3 has a certain extra length between head 1 and eyepiece member 5, so that the elements can correspondingly yield on pivoting about angle $\alpha$. Hinge 2 can be constructed in such a way that a pivot angle $\alpha$ of more than 80° is possible.

FIG. 2 is a plan view of the instrument according to FIG. 1. It is in particular possible to see that hinge 2 is constructed in a conventional manner, which need not be shown in greater detail, because hinges of wide variety are well-known. It can be very easy to move the hinge, because it can be adjusted by corresponding hinge screws. There is also no need to show this in detail, because, once again, known variants are possible in connection with hinges.

The doctor first introduces the distal end 9 of the shaft 4 into the patient's larynx, while viewing through eyepiece 8. Further insertion is easy for the doctor, because he can vary the angle $\alpha$ in random manner by hand and consequently can easily yield to the movements of rigid head 1. There is no significant change to the image 8 received in the eyepiece, even if there is a very considerable variation to angle $\alpha$.

Thus, the invention permits much easier manipulations on the part of the doctor. It is also possible to use some other joint instead of the shown hinge, i.e., a ball and socket joint.

I claim:

1. An instrument comprising: a flexible light guide element and a flexible image-transmitting element, both having a distal end; a head receiving and connecting to said elements; an eyepiece member connected to said image-transmitting element; and a line-axis hinge joining said head and said eyepiece member, said image-transmitting element extending to said distal end and including a flexible portion disposed between said eyepiece member and said head or said length, which is not restrained by either said head or said eyepiece member, to enable them to be pivoted relative to one another, the hinge enabling a torque exerted on the eyepiece member to rotate the head, and a torque on the head to rotate the eyepiece member, but relative rotation of the head and eyepiece member being limited to movement in a plane normal to said hinge.

2. An instrument according to claim 1 adapted to function also as an anesthetic catheter, including channel means to convey intubation gas through said head and along said light guide element.

3. An instrument according to claim 1 in which said image-transmitting member is also flexible between said head and its said distal end.

4. An instrument according to claim 3 adapted to function also as an anesthetic catheter, including channel means to convey intubation gas through said head and along said light guide element.

* * * * *